US011100912B2

(12) United States Patent
McCutcheon

(10) Patent No.: US 11,100,912 B2
(45) Date of Patent: Aug. 24, 2021

(54) NOISE CANCELLATION HEADPHONE

(71) Applicant: ams International AG, Rapperswil (CH)

(72) Inventor: Peter McCutcheon, Rapperswil (CH)

(73) Assignee: AMS INTERNATIONAL AG, Rapperswil (CH)

( * ) Notice: Subject to any disclaimer, the term of this patent is extended or adjusted under 35 U.S.C. 154(b) by 0 days.

(21) Appl. No.: 16/640,827

(22) PCT Filed: Aug. 16, 2018

(86) PCT No.: PCT/EP2018/072234
§ 371 (c)(1),
(2) Date: Feb. 21, 2020

(87) PCT Pub. No.: WO2019/038178
PCT Pub. Date: Feb. 28, 2019

(65) Prior Publication Data
US 2021/0043184 A1 Feb. 11, 2021

(30) Foreign Application Priority Data
Aug. 23, 2017 (EP) .................................... 17187524

(51) Int. Cl.
*A61F 11/06* (2006.01)
*G10K 11/16* (2006.01)
*H03B 29/00* (2006.01)
*G10K 11/178* (2006.01)
*H04R 1/10* (2006.01)

(52) U.S. Cl.
CPC ......... *G10K 11/17857* (2018.01); *H04R 1/10* (2013.01); *G10K 2210/506* (2013.01); *H04R 2460/01* (2013.01)

(58) Field of Classification Search
CPC ............................ G10K 11/17857; H04R 1/10
See application file for complete search history.

(56) References Cited

U.S. PATENT DOCUMENTS 4,494,074 A 1/1985 Bose
4,852,177 A 7/1989 Ambrose
5,182,774 A 1/1993 Bourk
5,675,658 A * 10/1997 Brittain .................. A61F 11/14 381/186
7,466,838 B1 * 12/2008 Moseley .......... G10K 11/17857 381/370
2009/0010474 A1 * 1/2009 Ouryouji .............. H04R 1/1083 381/370
2016/0330537 A1 11/2016 Barrentine et al.

FOREIGN PATENT DOCUMENTS

GB 2234882 2/1991
WO WO-2016037067 A1 * 3/2016 ........... H04R 1/1075

OTHER PUBLICATIONS

European Patent Office, International Search Report for PCT/EP2018/072234 dated Oct. 18, 2018.

* cited by examiner

*Primary Examiner* — Simon King
(74) *Attorney, Agent, or Firm* — MH2 Technology Law Group LLP

(57) ABSTRACT

A noise cancellation headphone comprises a speaker, a front plate for carrying the speaker, a microphone arranged on or in the front plate, and a front vent opening arranged within the front plate and in close proximity to the microphone. The microphone is usable as a feedback microphone for active noise cancellation.

21 Claims, 3 Drawing Sheets

NOISE CANCELLATION HEADPHONE

BACKGROUND OF THE INVENTION

The present disclosure relates to a noise cancellation headphone.

Nowadays a significant number of headphones are equipped with noise cancellation techniques. For example, such noise cancellation techniques are referred to as active noise cancellation or ambient noise cancellation, both abbreviated with ANC. ANC generally makes use of recording ambient noise that is processed for generating a compensation signal or anti-noise signal, which is then combined with a useful audio signal to be played over a speaker of the headphone.

Various ANC approaches make use of feedback, FB, microphones, feedforward, FF, microphones or a combination of feedback and feedforward microphones.

Traditionally, feedback cancellation is tuned to produce optimum noise cancellation at the feedback microphone. This approach is chosen because a feedback system relies upon monitoring the cancelled signal to work, so it follows that it is optimized at this point. However, humans hear the signal at a slightly different point, namely the eardrum. This point is often referred to as the drum reference point, DRP. Nevertheless, it is often considered acceptable to ignore any differences in noise cancellation between the FB microphone and the DRP.

SUMMARY OF THE INVENTION

The present disclosure provides an improved concept for noise cancellation in a headphone employing a feedback microphone that improves noise reduction performance.

It has been found that at very low frequencies, where the wavelength of sound is much greater than the distance between the feedback microphone and the DRP, the signal at the feedback microphone is comparable to the signal at the DRP. Due to the speaker response in a feedback noise cancelling headphone, the cancellation is typically limited to low frequencies, e.g. below 1 kHz. Therefore, conventional approaches accept that any differences in noise cancellation between the FB microphone and the DRP can be ignored.

However, the position of the DRP and the feedback microphone are different. It has been found by the inventor that as the anti-noise signal from the speaker creates an optimized null at the feedback microphone, the anti-noise signal continues to propagate to the DRP. It can then be appreciated that the anti-noise signal from the speaker combines with the noise signal at the ear to produce a different combined signal, having a potentially worse cancellation performance.

The improved concept is based on the idea of placing of acoustic components like microphone, speaker and vents such that a difference in superposition of the anti-noise signal and the noise signal at the DRP and the feedback microphone are minimized. In particular, this is achieved by placing a headphone front vent in a front plate of the headphone in close proximity to the feedback microphone. By such placement, the noise cancellation at the ear will be very similar to the noise cancellation at the feedback microphone. This is contrary to conventional headphone design, where the feedback microphone is placed close to the center of the speaker to minimize propagation delays from the speaker to the microphone and is therefore not close to the front vent. The feedback ambient noise cancellation, FB ANC, at the FB microphone and at the ear are therefore different.

In some implementations, the improved concept with the FB microphone in close proximity to the front vent goes further by adding a baffle to delay the ambient to ear path. In particular, the baffle delays the noise entering the headphone via the vent before being detected at the ear. Essentially this improves the feedback noise cancellation bandwidth at the ear compared to that at the feedback microphone. In this scenario, it so happens that the ANC at the DRP can be even superior to that at the FB microphone.

An embodiment of a noise cancellation headphone according to the improved concept comprises a speaker, a front plate for carrying the speaker, a microphone arranged on or in the front plate, and a front vent opening arranged within the front plate and in close proximity to the microphone. The microphone is usable as a feedback microphone for active noise cancellation. The front vent opening allows a controllable path by which ambient noise from outside the headphone can reach the inside of the headphone, in particular the feedback microphone.

In some implementations the microphone is arranged in close proximity to the speaker, for example close to an edge of the speaker, respectively the speaker's membrane.

Similarly, in some implementations the front vent opening is arranged in close proximity to the speaker, for example close to an edge of the speaker, respectively the speaker's membrane.

In some implementations, the front vent opening is arranged in close proximity to the feedback microphone.

For example, the front vent opening is or provides an acoustic pathway, with or without an acoustic resistor, from a front volume, e.g. an air volume between the speaker and a user's ear, to the ambient environment. This is either from the front volume in front of the speaker to the rear volume behind the speaker and out to the ambient environment, or it is directly to the ambient environment.

Hence, in some implementations the front vent opening creates an acoustic couple or pathway between the air volume in front of the speaker and the ambient environment. In other implementations, the front vent opening creates an acoustic couple between the air volume in front of the speaker and the air volume behind the speaker. In this case, the air volume behind the speaker is acoustically coupled to the ambient environment through a second vent.

Preferably the front vent opening provides the only airborne acoustic pathway from the ambient environment to the front volume in front of the speaker. Airborne for instance excludes a pathway through the speaker or the speaker membrane.

Accordingly, the front vent opening provides a dominant source of ambient noise, e.g. in a frequency band of the ANC.

For example, a distance between the front vent opening and the microphone is less than 10 mm, e.g. less than 5 mm. However, the distance between the front vent opening, e.g. an edge of the front vent opening, and the microphone, e.g. the microphone's inlet port, is chosen to be as small as possible and may only be limited mechanically by a fixation of the microphone in or on the front plate.

For example, a distance between the microphone and the front vent opening is equal to or smaller than a distance between the microphone and a center of the speaker, e.g. a center of a speaker driver or coil of the speaker.

In some implementations the front vent opening has a cross sectional area between 0.1 and 100 $mm^2$, e.g. between 5 and 50 $mm^2$.

In some implementations the front vent opening has an acoustic mass between 40 and 500,000 $kg/m^4$, e.g. between 40 and 9000 $kg/m^4$. Where acoustic mass $M_A$ is defined as follows:

$$M_A = \frac{\rho_0 l}{\pi a^2}$$

Where $\rho_0$ is the ambient density of air, l is the length of the vent, π is the mathematical constant and a is the cross sectional area of the vent.

In some implementations the vent is covered by a resistive mesh having an acoustic resistance between 30 and 300 Rayls, e.g. between 100 and 160 Rayls, where Rayls is the specific acoustic impedance [MKS].

The size of the front vent opening may also depend on the size of the front plate, respectively the speaker properties, and/or an air volume formed in front of the speaker by the headphone. In particular, larger headphones, respectively speakers, can operate with larger openings.

In further implementations of the improved concept the headphone further comprises a baffle. For example, the speaker has a frontside facing a user's ear, in particular during operation of the headphone, the frontside being opposite to a backside of the speaker. The baffle is arranged over the front vent opening and at least partially covers the speaker on the frontside. For example, the baffle is also arranged over the microphone.

Preferably the baffle is made from an acoustically opaque material. Such acoustically opaque material ensures that sound does not go through the baffle but has to follow an acoustic path around the baffle. The baffle e.g. is made from the acoustically opaque material along its whole profile, i.e. without gaps or holes in its surface.

According to the improved concept the baffle has the function of delaying ambient signals entering the headphone through the front vent opening on their way to the user's ear. It should be noted, however, that the acoustic path for the ambient noise signals to the microphone, from the speaker driver to the ear and from the speaker driver to the microphone, are not changed. Accordingly, particularly the higher frequency components of the feedback noise cancellation are extended, therefore improving the ANC performance in the high frequency band. It should be noted that in some implementations this comes into effect for frequencies higher than about 200 Hz.

In some implementations the baffle is arranged in parallel or basically in parallel to the frontside of the speaker and/to the front plate. Accordingly, slight deviations from a parallel arrangement are also encompassed.

In some implementations a shape of the baffle at least partially, e.g. for the most part, is framed by an arc of an ellipse, e.g. of a circle. A part of the shape of the baffle that has a different shape may, for example, be limited by a shape of the front plate and/or a housing of the headphone. Preferably a center of the ellipse, respectively the circle, is centred over or basically over the feedback microphone. This facilitates that a distance between the feedback microphone and an edge of the baffle is more or less constant.

In some implementations an acoustic path, e.g. a length of the acoustic path, between the feedback microphone and open edge of the baffle is constant or basically constant over a circumference of the baffle. This may, for example, be achieved with the circle-like or ellipse-like shape described above. Other shapes providing the same function are also encompassed.

In some implementations a distance between the baffle and the front plate is less than 5 mm, e.g. less than 2 mm. Such a distance may be defined between a main surface of the front plate and a main surface of the baffle.

In some implementations the baffle has a plane body, in particular on the side facing the front vent opening, respectively the front plate. For example, the baffle, e.g. the plane body of the baffle is fixed to the front plate with a base element. Preferably the baffle is designed and/or fixed such that it does not mechanically resonate, in particular during operation. For example, a resonant frequency of the baffle is outside an audible frequency spectrum.

For example, the base element runs along an edge of the baffle at all points where a distance from the feedback microphone to the edge of the baffle is less than a maximum distance from the feedback microphone to the edge of the baffle. Preferably, the base element is acoustically opaque in such implementation.

In various implementations the headphone is designed as an over-ear headphone or circumaural headphone. However, the improved concept can also be applied to on-ear headphones or in-ear headphones employing feedback noise cancellation.

BRIEF DESCRIPTION OF THE DRAWINGS

The improved concept will be described in more detail in the following with the aid of drawings. Elements having the same or similar function bear the same reference numerals throughout the drawings. Hence their description is not necessarily repeated in following drawings.

In the drawings.

DETAILED DESCRIPTION

Figure 1:
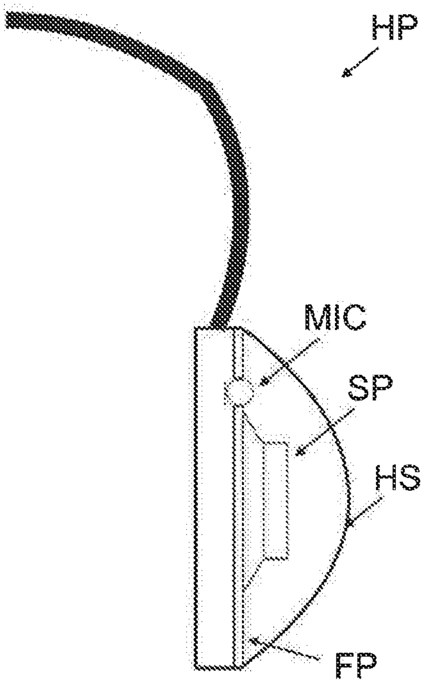
FIG. 1 shows a schematic view of a headphone.

FIG. 1 shows a schematic view of a headphone HP that in this example is designed as an over-ear or circumaural headphone. Only a portion of the headphone HP is shown, corresponding to a single audio channel. However, extension to a stereo headphone will be apparent to the skilled reader. The headphone HP comprises a housing HS carrying a front plate FP which itself carries a speaker SP and a microphone MIC. The microphone MIC is designed as a feedback noise microphone for recording ambient noise for active noise cancellation or reduction techniques. The microphone MIC is e.g. directed or arranged such that it records both ambient noise and sound played over the speaker SP. For instance the microphone MIC is arranged in close proximity to the speaker, for example close to an edge of the speaker SP or to the speaker's membrane. Furthermore, the headphone HP comprises a front vent opening arranged within the front plate FP and in close proximity to the microphone MIC. The front vent opening is not visible in FIG. 1 due to the perspective chosen in FIG. 1.

Figure 2:
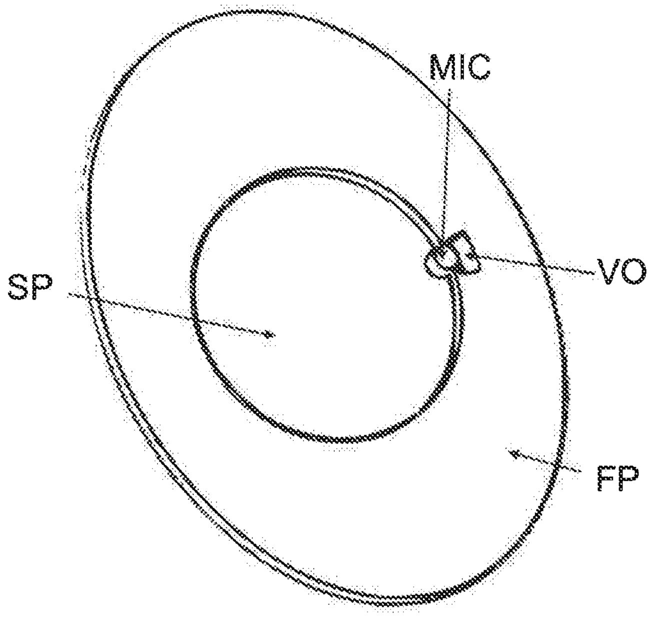
FIG. 2 shows an example detail of a headphone.

Referring now to FIG. 2, a schematic perspective view of the front plate FP with the speaker SP and the microphone MIC is shown. Furthermore, the front vent opening VO is visible in the drawing of FIG. 2, being arranged in close proximity to the microphone MIC. FIG. 2 particularly shows the front side of the speaker SP, respectively the front plate FP, that is the side facing a user's ear during operation of the headphone.

The front vent opening VO generally has the basic function of allowing a release of pressure built up in the front volume of the headphone which may occur as a result of placing the headphones on the head. Without such a vent, the speaker risks being damaged.

According to the improved concept, the positioning or placement of the front vent opening VO in close proximity to the microphone MIC ensures that ambient sound or noise from the backside of the headphone, respectively from outside the headphone, passes the feedback microphone as it propagates to the ear. Directing the noise via this path reduces a difference between the compensation results at the feedback microphone and at the drum reference point, DRP, at the user's ear-drum. In particular, the placement of the microphone in relation to the front vent opening achieves that the source of the noise entering the ear travels via the feedback microphone in the same or similar manner that the signal from the speaker does. In such a configuration the noise cancellation at the ear, respectively the DRP, and at the feedback microphone MIC are more or less the same. For example, the front vent opening VO is or provides an acoustic pathway, with or without an acoustic resistor, from a front volume, e.g. an air volume between the speaker SP and a user's ear, to the ambient environment. This is either from the front volume in front of the speaker to the rear volume behind the speaker and out to the ambient environment, or it is directly to the ambient environment.

Preferably, the front vent opening VO provides the only airborne acoustic pathway from the ambient environment to the front volume in front of the speaker. Therefore, the front vent opening provides a dominant source of ambient noise, e.g. in a frequency band of the ANC.

Figure 3A:
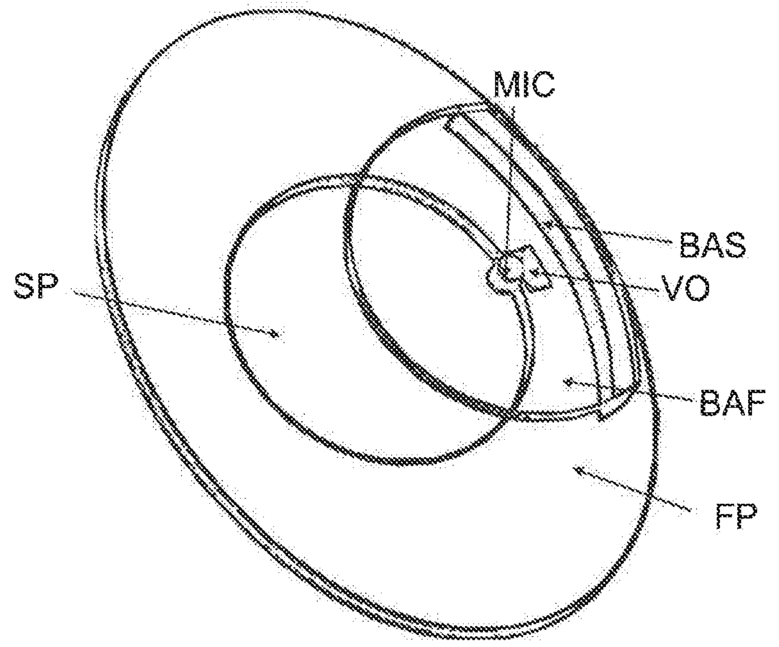
FIGS. 3A and 3B show further example details of a headphone.
Figure 3B:
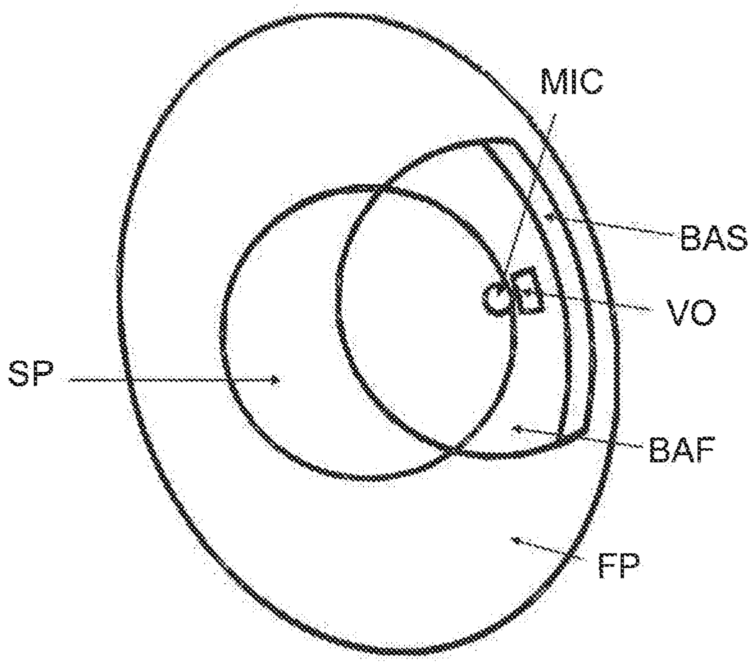

FIGS. 3A and 3B shows a development of the embodiment of FIG. 2. FIG. 3A shows a more perspective view of the arrangement, while FIG. 3B shows a more schematic view of the arrangement. In addition to the arrangement of FIG. 2, a baffle BAF is arranged over the front vent opening VO and at least partially covers the speaker SP on the frontside. The baffle BAF is shown as a transparent member for reasons of a better visibility only. In practical implementations a transparency of the baffle for light has no function, so the baffle BAF can also be opaque for light. However, preferably the baffle is made from an acoustically opaque material such that sound entering through the front vent opening VO cannot go directly through the baffle BAF but has to go along its main surface to reach an open edge of the baffle BAF.

A shape of the baffle BAF for the most part is framed by an arc of an ellipse, respectively a circle. The center of the circle, respectively ellipse, is arranged over or basically over the feedback microphone MIC. Accordingly, an acoustic path from the front vent opening VO to the open edge, respectively circumference of the baffle BAF, is constant or basically constant over the circumference of the baffle BAF. It should be noted that the same or similar functionality could be achieved if the outer shape of the baffle BAF was not in a perfect shape but structured with waves, teeth or other small shapes varying the general elliptic or circular shape.

As can be seen from FIGS. 3A and 3B, the baffle BAF has a plane body, at least on the side facing the microphone and facing the front vent opening VO. The baffle BAF in this example is fixed to the front plate FP with a base element BAS. However, other kinds of fixation of the baffle BAF to the front plate FP are encompassed. Moreover, baffle BAF and base element BAS could be formed as a single piece. It is important to note that in cases where the distance from the microphone to the base element BAS is less than the distance from the microphone to the circumference of the baffle BAF, then the base element BAS is acoustically opaque such that sound cannot travel beyond the base element BAS.

Figure 4:
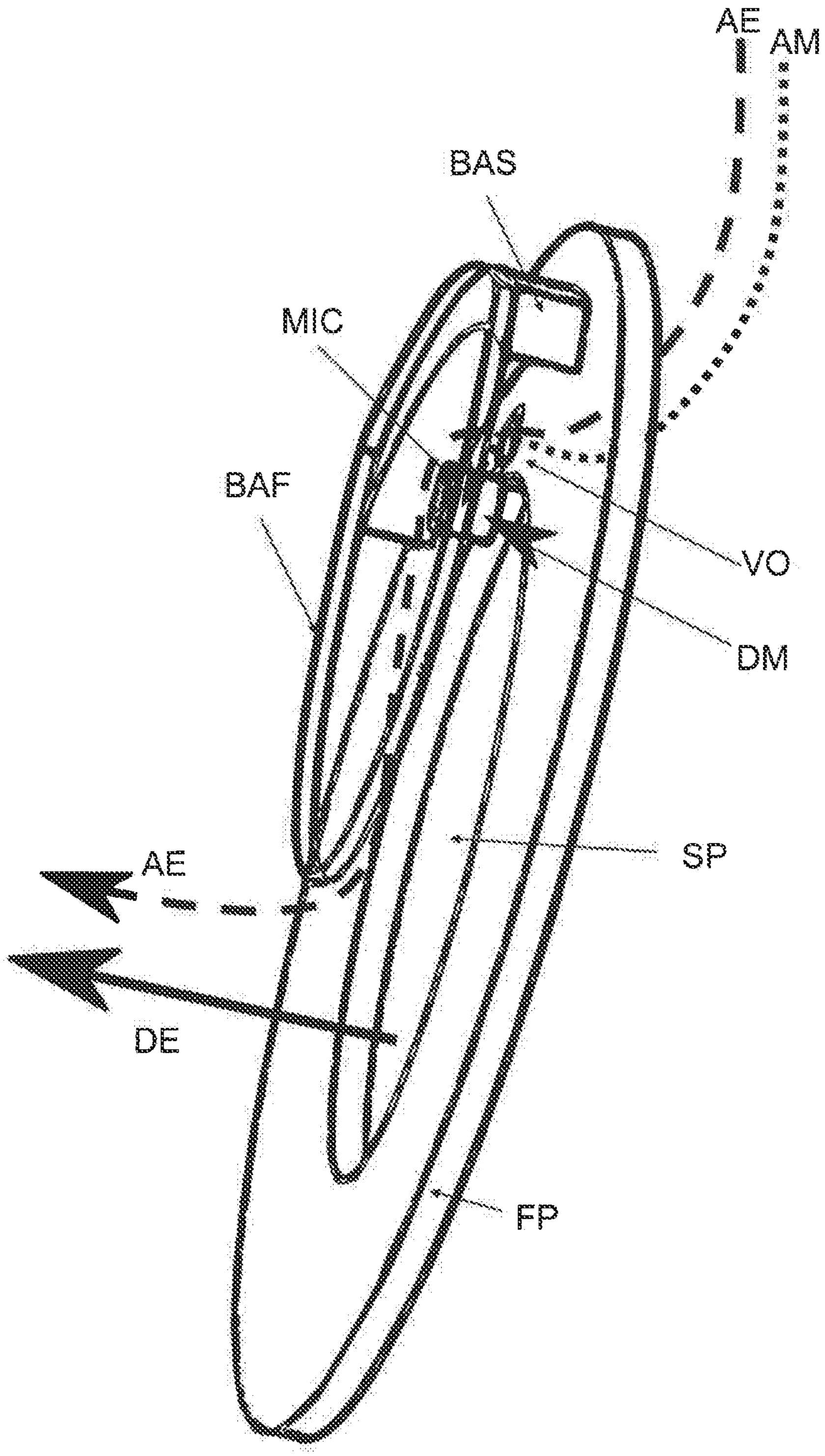
FIG. 4 shows an example of acoustic paths in a detail of a headphone.

Referring now to FIG. 4, a perspective side view of the arrangement of FIGS. 3A and 3B is shown together with various signal paths for explaining the function of the baffle BAF in more detail.

In particular, four different signal paths are shown in the drawing of FIG. 4, two originating from an ambient noise or sound source, and two originating from the speaker driver. For example, the sound path AE represents an ambient to ear sound path that goes from the ambient noise source from the backside of the front plate FP through the front vent opening VO, below the baffle BAF up to its open edge, and finally to the ear drum of the user. It can be specifically seen that the sound path AE is delayed by the baffle BAF compared to a possible arrangement without the baffle BAF.

The sound path AM represents the sound path from the ambient noise source to the microphone MIC and goes from the backside of the front plate FP through the vent opening VO directly to the microphone MIC.

The sound path DM goes from the speaker driver directly to the microphone MIC that is arranged above the speaker driver. The sound path DE represents the path from the driver to the user's eardrum.

The additional delay introduced by the baffle for the signal path AE supports improving the performance of the ambient noise cancellation, respectively ambient noise reduction at the user's ear or drum reference point, DRP.

In particular, the delay of the AE signal path extends the feedback noise cancellation performance at the DRP for higher frequencies.

The improved concept has been described in conjunction with an over-ear, respectively circumaural headphone. However, the proposed placement of the front vent opening with respect to the feedback microphone and, optionally, provision of the baffle can also be employed for other types of headphones like over-ear headphones or in-ear headphones, adapting the spatial dimensions where necessary.

The invention claimed is:

1. A noise cancellation headphone, comprising:

a speaker;

a front plate for carrying the speaker;

a microphone arranged on or in the front plate, the microphone being usable as a feedback microphone for active noise cancellation; and a front vent opening arranged within the front plate and in close proximity to the microphone, wherein a distance between the front vent opening and the microphone is less than 10 mm, in particular less than 5 mm.

2. The headphone according to claim 1, wherein the front vent opening creates an acoustic couple or pathway between an air volume in front of the speaker and an ambient environment outside the headphone, in particular outside a housing of the headphone.

3. The headphone according to claim 2, wherein the front vent opening creates the acoustic couple or pathway according to one of the following:

directly between the air volume in front of the speaker and the ambient environment;

between the air volume in front of the speaker and an air volume behind the speaker, wherein the air volume behind the speaker is acoustically coupled to the ambient environment through a further vent opening.

4. The headphone according to claim 2, wherein the front vent opening provides the only airborne acoustic pathway from the ambient environment to the front volume in front of the speaker.

5. The headphone according to claim 1, wherein the front vent opening provides a dominant source of ambient noise, in particular in a frequency band of the active noise cancellation.

6. The headphone according to claim 1, wherein the microphone is arranged in close proximity to the speaker, in particular close to an edge of the speaker.

7. The headphone according to claim 1, wherein the front vent opening is arranged in close proximity to the speaker, in particular close to an edge of the speaker or a membrane of the speaker.

8. The headphone according to one claim 1, wherein the front vent opening has an acoustic mass between 40 and 500,000 kg/$m^4$, in particular between 40 and 9000 kg/$m^4$.

9. The headphone according to claim 1, wherein the speaker has a frontside facing a user's ear and being opposite to a backside of the speaker, the headphone further comprising a baffle arranged over the front vent opening and at least partially covering the speaker on the frontside.

10. The headphone according to claim 9, wherein the baffle is made from an acoustically opaque material, in particular such that sound does not go through the baffle.

11. The headphone according to claim 9, wherein the baffle is arranged in parallel or basically in parallel to the frontside of the speaker and/or to the front plate.

12. The headphone according to claim 9, wherein a shape of the baffle at least partially, in particular for the most part, is framed by an arc of an ellipse, in particular of a circle.

13. The headphone according to claim 12, wherein a center of the ellipse is arranged over or basically over the front vent opening and the microphone.

14. The headphone according to claim 9, wherein an acoustic path between the front vent opening and an open edge of the baffle is constant or basically constant over a circumference of the baffle.

15. The headphone according to claim 9, wherein a distance between the baffle and the front plate is less than 5 mm, in particular less than 2 mm.

16. The headphone according to claim 9, wherein the baffle is fixed to the front plate with a base element.

17. The headphone according to claim 16, wherein the base element runs along an edge of the baffle at all points where a distance from the feedback microphone to the edge of the baffle is less than a maximum distance from the feedback microphone to the edge of the baffle.

18. A noise cancellation headphone, comprising:

a speaker;

a front plate for carrying the speaker;

a microphone arranged on or in the front plate, the microphone being usable as a feedback microphone for active noise cancellation; and a front vent opening arranged within the front plate and in close proximity to the microphone, wherein a distance between the microphone and the front vent opening is equal to or smaller than a distance between the microphone and a center of the speaker, in particular a center of a speaker driver or coil of the speaker.

19. The headphone according to claim 18, wherein the speaker has a frontside facing a user's ear and being opposite to a backside of the speaker, the headphone further comprising a baffle arranged over the front vent opening and at least partially covering the speaker on the frontside.

20. A noise cancellation headphone, comprising:

a speaker;

a front plate for carrying the speaker;

a microphone arranged on or in the front plate, the microphone being usable as a feedback microphone for active noise cancellation; and a front vent opening arranged within the front plate and in close proximity to the microphone, wherein the front vent opening has a size between 0.1 and 100 $mm^2$, in particular between 5 and 50 $mm^2$.

21. The headphone according to claim 20, wherein the speaker has a frontside facing a user's ear and being opposite to a backside of the speaker, the headphone further comprising a baffle arranged over the front vent opening and at least partially covering the speaker on the frontside.

* * * * *